United States Patent [19]
Winston et al.

[11] Patent Number: 6,159,449
[45] Date of Patent: *Dec. 12, 2000

[54] DENTIFRICE PRODUCTS AND METHODS FOR REMINERALIZING AND/OR MINERALIZING TEETH

[75] Inventors: Anthony E. Winston, East Brunswick; Norman Usen, Marlboro, both of N.J.

[73] Assignee: Enamelon, Inc., East Brunswick, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/832,827

[22] Filed: Apr. 3, 1997

[51] Int. Cl.$^7$ .................................. A61K 7/16; A61K 7/18
[52] U.S. Cl. .................................. 424/52; 424/49; 424/57
[58] Field of Search .......................... 424/49–58

[56] References Cited

U.S. PATENT DOCUMENTS

| | | | |
|---|---|---|---|
| 2,627,493 | 2/1953 | Merckel et al. | 167/93 |
| 2,700,012 | 1/1955 | Merckel et al. | 167/93 |
| 3,679,360 | 7/1972 | Rubin et al. | 23/109 |
| 3,728,446 | 4/1973 | Roberts et al. | 424/49 |
| 3,966,901 | 6/1976 | Cullum et al. | 424/52 |
| 4,048,300 | 9/1977 | Tomlinson et al. | 424/52 |
| 4,075,317 | 2/1978 | Mitchell et al. | 424/52 |
| 4,080,440 | 3/1978 | DiGiulio et al. | 424/49 |
| 4,083,755 | 4/1978 | Grabenstetter et al. | 424/49 |
| 4,083,955 | 4/1978 | Grabenstetter et al. | 424/49 |
| 4,141,969 | 2/1979 | Mitchell | 424/52 |
| 4,150,112 | 4/1979 | Wagenknecht et al. | 424/48 |
| 4,159,280 | 6/1979 | Wason | 424/52 |
| 4,159,315 | 6/1979 | Wagenknecht et al. | 424/48 |
| 4,177,258 | 12/1979 | Gaffar et al. | 424/52 |
| 4,183,915 | 1/1980 | Gaffar et al. | 424/52 |
| 4,233,288 | 11/1980 | Cornell | 424/48 |
| 4,244,707 | 1/1981 | Wason | 51/308 |
| 4,265,877 | 5/1981 | Tenta | 424/48 |
| 4,280,822 | 7/1981 | Wason | 51/308 |
| 4,283,385 | 8/1981 | Dhabhar et al. | 424/52 |
| 4,340,584 | 7/1982 | Wason | 424/52 |
| 4,348,381 | 9/1982 | Gaffar et al. | 424/52 |
| 4,397,837 | 8/1983 | Raaf et al. | 424/51 |
| 4,412,983 | 11/1983 | Mitchell | 424/52 |
| 4,460,565 | 7/1984 | Weststrate et al. | 424/52 |
| 4,565,691 | 1/1986 | Jackson | 424/52 |
| 4,606,912 | 8/1986 | Rudy et al. | 424/52 |
| 4,610,873 | 9/1986 | Rudy et al. | 424/52 |
| 4,672,032 | 6/1987 | Slavkin et al. | 435/68 |
| 4,714,608 | 12/1987 | Rolla | 424/52 |
| 4,824,681 | 4/1989 | Schobel et al. | 426/5 |
| 4,923,683 | 5/1990 | Sakuma et al. | 424/52 |
| 4,983,379 | 1/1991 | Schaeffer | 424/52 |
| 5,037,639 | 8/1991 | Tung | 424/57 |
| 5,045,305 | 9/1991 | Clarkson et al. | 424/52 |
| 5,047,031 | 9/1991 | Constantz | 606/77 |
| 5,124,160 | 6/1992 | Zibell et al. | 426/3 |
| 5,129,905 | 7/1992 | Constantz | 606/76 |
| 5,139,769 | 8/1992 | Gaffar et al. | 424/52 |
| 5,268,167 | 12/1993 | Tung | 424/52 |
| 5,378,131 | 1/1995 | Greenberg | 424/440 |
| 5,424,059 | 6/1995 | Prencipe et al. | 424/52 |
| 5,427,768 | 6/1995 | Tung | 424/52 |
| 5,437,857 | 8/1995 | Tung | 424/52 |
| 5,460,803 | 10/1995 | Tung | 424/57 |
| 5,476,647 | 12/1995 | Chow et al. | 424/52 |
| 5,571,502 | 11/1996 | Winston et al. | 424/52 |
| 5,603,922 | 2/1997 | Winston et al. | 424/49 |
| 5,605,675 | 2/1997 | Usen et al. | 424/49 |
| 5,605,677 | 2/1997 | Schumann et al. | 424/52 |
| 5,614,175 | 3/1997 | Winston et al. | 424/52 |
| 5,645,853 | 7/1997 | Winston et al. | 424/448 |
| 5,785,956 | 7/1998 | Sullivan et al. | 424/52 |
| 5,817,296 | 10/1998 | Winston et al. | 424/57 |
| 5,833,957 | 11/1998 | Winston et al. | 424/57 |
| 5,858,333 | 1/1999 | Winston et al. | 424/57 |
| 5,958,380 | 9/1999 | Winston et al. | 424/57 |
| 6,036,944 | 3/2000 | Winston et al. | 424/57 |

FOREIGN PATENT DOCUMENTS

WO 94/18938    1/1994    WIPO.

OTHER PUBLICATIONS

"Electrical Resistance Measurements of Demineralized Enamel after In Vitro Remineralizing Treatments", N.D.Y. Gnagne–Agnero et al, J Dent Res 76 (IADR Abstracts) 1997, 1931.

"Remineralization by Fluoride Enhanced with Calcium and Phosphate Ingredients", B.R. Schemehorn et al, J Dent Res 76 (IADR Abstracts) 1997, 2897.

"Remineralization by A Novel Dentifrice", J.M. Tanzer et al, J Dent Res 76 (IADR Abstracts) 1997, 965.

*Primary Examiner*—Shep K. Rose
*Attorney, Agent, or Firm*—Stuart D. Frenkel

[57] ABSTRACT

A dentifrice product substantially free of water-soluble inorganic orthophosphates and capable of remineralizing subsurface lesions and/or mineralizing exposed dentinal tubules in teeth, contains (A) a discrete cationic part containing at least one water-soluble and/or partially water-soluble calcium compound and a fluoride-protecting amount of at least one water-soluble and/or partially water-soluble magnesium compound, and (B) a discrete anionic part containing at least one water-soluble fluoride compound. The cationic and anionic parts are disposed separate from one another in the product and are simultaneously releasable from the product. The cationic and anionic parts each have a pH in water such that a mixed aqueous composition formed by mixing the cationic and anionic parts with (i) saliva or (ii) water and saliva has a pH of from about 4.0 to about 10.0. The mixed aqueous composition simultaneously applies the cationic and anionic parts to the tooth surfaces being treated. Dentifrice products containing a minor amount of at least one water-soluble inorganic orthophosphate compound in the anionic part and dentifrice products which are substantially devoid of water-soluble inorganic orthophosphate compounds but which may contain a substantially water-insoluble phosphate compound, e.g., as an abrasive and/or polishing agent, are also provided.

28 Claims, No Drawings

DENTIFRICE PRODUCTS AND METHODS FOR REMINERALIZING AND/OR MINERALIZING TEETH

BACKGROUND OF THE INVENTION

This invention relates to dentifrice products and methods for remineralizing and/or mineralizing teeth. More particularly, this invention relates to fluoride-containing dentifrice products and methods of using same to achieve improved remineralization of subsurface carious lesions and/or mineralization of exposed dentinal tubules.

Dental caries, i.e., tooth decay, is a leading cause of tooth damage in humans. Dental caries begins with lesions of so-called "white spots", which are demineralized areas below the surface of intact dental enamel. Such subsurface lesions are formed before a cavity is detectable. If unchecked, surface enamel above a subsurface lesion eventually collapses, leading to cavitation and subsequent loss of tooth structure.

Dental caries is typically caused by the presence of acids in the oral cavity. This is because the primary component of the enamel and dentin in teeth is calcium hydroxyapatite, which, though highly insoluble at normal oral pHs, is relatively soluble in acid media. Thus, when a tooth is exposed to acids, e.g., acids formed during the glycolysis of sugar caused by various oral bacteria, carious lesions can form in the enamel and dentin of the tooth.

Compositions and methods for preventing or reducing dental caries are known in the art. Reference is made, for example, to U.S. Pat. Nos. 3,966,901 (Cullum et al.): 4,714,608 (Rolla); 4,233,288 (Cornell); 5,129,905 and 5,407,031 (both to Constantz); 4,075,317 (Mitchell); and 2,700,012 and 2,627,493 (both to Merckel et al.).

Although it is desirable to prevent caries from spreading, it is also desirable to restore the carious tooth to its original state. Restoration of a carious tooth to its original state involves the process of remineralization. The object of remineralization is to deposit hydroxyapatite in the carious lesion such that the dental enamel incorporates the hydroxyapatite into its structure at the point of lesion. Thus, remineralization not only prevents further tooth decay but also restores the tooth to its original state.

Compositions and methods which use remineralization to retard or arrest dental caries are known in the art. Reference is made, for example, to U.S. Pat. Nos. 4,080,440 (Digiulio et al); 4,177,258, 4,183,915 and 4,348,381 (Gaffar et al); 4,083,955 (Grabenstetter et al); 4,397,837 (Raaf et al); 4,606,912 (Rudy et al.); 3,679,360 (Rubin et al.); 5,037,639; 5,268,167; 5,437,857; 5,427,768; and 5,460,803 (all to Tung); and 5,605,677 (Schumann et al). Reference is also made to U.S. Pat. Nos. 5,603,922 (Winston et al.); 5,605,675 (Usen et al.); and 5,571,502 (Winston et al.), and to commonly assigned U.S. Pat. No. 5,645,853.

U.S. Pat. No. 4,080,440 (Digiulio et al) discloses a method for remineralizing tooth enamel involving forming a metastable mixture having a low pH (between 2.5 and 4.0) by mixing a solution containing a soluble calcium salt and preferably a soluble salt of a heavy metal or magnesium with a solution containing a soluble phosphate salt and preferably a soluble fluoride salt, and then applying the metastable mixture to the tooth surface. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et al) disclose a remineralizing solution containing supersaturated concentrations of calcium ions, phosphate ions and a fluoride source stabilized by the present of an antinucleating agent such as diamine tetramethylenephosphonic acid, ethylenediamine tetramethylenephosphonic acid and 2-phosphonobutane-tricarboxylic acid-1,2,4, or the water-soluble salts thereof. This solution is preferably adjusted to the neutral pH range where the solution is alleged to most effectively remineralize subsurface lesions. Even though the antinucleating agent would be expected to stabilize the solution, equilibrium of the supersaturated concentrations is still found difficult to maintain and avoid precipitation of hydroxyapatite and changes in the pH of the solution.

U.S. Pat. Nos. 4,083,955 (Grabenstetter et al) and 4,397,837 (Raaf et al) disclose a process for remineralizing demineralized enamel by the consecutive treatment of tooth surfaces with separate solutions containing calcium ions and phosphate ions. In this process, the solution containing the calcium ions may further contain heavy metal ions or magnesium ions, while the solution containing the phosphate ions may also contain fluoride ions. By sequentially applying calcium and phosphate ions to the tooth surface, high concentrations of the ions are able to penetrate into lesions in solution form, where the ions precipitate as a calcium phosphate salt when ions from the second treatment solution diffuse in. While apparently successful, this method involves the inconvenience of a plurality of sequential applications, which can also be time consuming.

U.S. Pat. Nos. 4,606,912 and 4,610,873 (Rudy et al.) teach methods of making clear aqueous mouthwash solutions which totally prevent formation of calcium phosphate crystals, e.g., hydroxyapatite. The solutions are capable of remineralizing lesions in teeth and are prepared by initially forming a solution containing a source of calcium ions and a chelating agent for calcium ions, causing the chelation of at least 50% of the calcium ions and subsequently adding a source of phosphate ions to the aqueous solution. Here too, while somewhat effective, the addition and necessary control of the amount of chelating agent makes the concept impractical.

U.S. Pat. No. 3,679,360 to Rubin et al. discloses a remineralization method the purpose of which is to deposit calcium phosphate from a gel medium onto the surface of a tooth. This method of remineralization has several disadvantages. For example, in the Rubin et al. method, remineralization occurs only on the surface of a tooth whereas the initial cause of dental caries is subsurface demineralization. Furthermore, in the Rubin et al. method, the surface on which apatite growth is desired must be prepared (as by roughening), and the tooth and coatings must be covered by a suitable cap for several days while the mineralization of the tooth surface occurs.

U.S. Pat. Nos. 5,037,639; 5,268,167; 5,437,857; 5,427,768; and 5,460,803 (all to Tung) teach the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite). In the Tung patents, remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

The aforementioned patents to Tung also teach the use of two-part solutions wherein a first part contains phosphate salt(s) and a second part contains calcium salts(s), wherein either the first part or the second part further contains carbonate salt(s). In addition, the Tung patents teach solutions formed by dissolving in water a solid powder containing calcium salt(s). These solutions are salt(s), and carbonate salt(s). These solutions are then applied to dental tissue. The Tung patents further teach the use of non-carbonated solid powders containing mixtures of calcium salts and phosphate salts which can be applied directly to the tooth or dispersed in gel, chewing gum, or other non-aqueous medium such as toothpaste which is placed in contact with the tooth. The patents teach that these powders are easily dissolved in saliva and then reprecipitated as an amorphous calcium phosphate compound. However, the Tung patents do not disclose the pHs of aqueous solutions formed from the non-carbonated solid powders.

U.S. Pat. No. 5,605,677 (Schumann et al.) discloses a toothpaste containing polishes, fluorine compounds, humectants, binders, and water, wherein the toothpaste is characterized in that it contains a combination of silica and dicalcium phosphate dihydrate at a weight ratio of 10:1 to 1:1 as the polishing component. According to the Schumann et al. patent, the toothpaste taught therein restores the surfaces of teeth by providing controlled remineralization, particularly in scratch marks and dentinal canals. Such remineralization renders these areas substantially level, leaving the teeth with a smooth continuous surface. Schumann et al. also teaches that the toothpaste therein may further contain magnesium ions and/or fluorophosphate ions. Schumann et al. does not disclose the presence of a water-soluble calcium compound in the toothpaste therein. Moreover, Schumann et al. does not teach the use of the magnesium ions to inhibit premature formation of calcium fluoride. The failure of Schumann et al. to teach this use of the magnesium ions therein is significant for reasons give hereinbelow.

U.S. Pat. No. 5,603,922 (Winston et al.) discloses one-part and two-part products and methods of using same to remineralize subsurface lesions. The one-part and two-part products contain at least one water-soluble calcium salt, at least one water-soluble divalent metal salt wherein the divalent metal is other than calcium and at least one water-soluble phosphate salt. The divalent metal is preferably magnesium, strontium, tin or zinc. In the two-part products, the calcium and divalent metal salts are disposed in a first discrete component, and the phosphate salt(s) is disposed in a second discrete component. The two-part product may further contain a dispensing means for allowing the first and second components to be simultaneously dispensed from the product so as to permit the dispensed first and second components to simultaneously contact the tooth or teeth being treated. The aqueous solution formed by mixing the salts used in the one-part and two-part products has a pH of from about 4.0 to about 7.0.

U.S. Pat. No. 5,605,675 (Usen et al.) discloses a two-part product and method of using same for remineralizing dental enamel, wherein the product contains a first discrete component composed of at least one water-soluble calcium salt and a second discrete component composed of at least one water-soluble phosphate salt and at least one water-soluble fluoride salt. The first and second components are simultaneously dispensable from the product and each have a pH in water such that when the two components are mixed to form an aqueous mixed solution, the solution has a pH of from about 4.5 and 10.0.

Commonly assigned U.S. Pat. No. 5,645,853 is directed to a chewing gum product and method of using same to remineralize subsurface lesions in teeth, wherein the chewing gum product contains a water-soluble cationic portion composed of at least one water-soluble calcium salt and at least one water-soluble divalent metal salt other than calcium salt; a water-soluble anionic portion containing at least one water-soluble phosphate salt; and a gum base. The divalent metal is preferably magnesium, strontium, tin or zinc. During chewing of the product, the anionic and cationic portions are simultaneously released into the water and/or saliva so as to form a mixed aqueous solution having a pH of from about 4.0 to 7.0.

U.S. Pat. No. 5,571,502 (Winston et al.) is directed to one-part, non-aqueous products and methods of using same to remineralize subsurface lesions, wherein the products contain at least one water-soluble calcium slat; at least one water-soluble phosphate salt; either a stabilizer or a hydrophilic, non-aqueous, water-soluble vehicle; and, optionally, at least one water-soluble fluoride salt. When the components are mixed with water or saliva to form an aqueous mixed solution, the solution has a pH of from about 4.5 to about 10.0.

Each of the products disclosed in the foregoing applications contains at least one water-soluble inorganic orthophosphate salt. For reasons discussed hereinbelow, it would be desirable to provide remineralizing/mineralizing dentifrice products which are substantially free of water-soluble inorganic orthophosphates.

Saliva itself helps protect teeth against demineralization and can slowly remineralize teeth which have become demineralized by acids. Because saliva is supersaturated with respect to calcium and phosphate ions, hydroxyapatite may be formed from substances occurring naturally in saliva. In the mouth, a natural equilibrium exists between the dissolution of hydroxyapatite from the teeth and the formation of hydroxyapatite on or in the teeth from the calcium and phosphate ions in the saliva. This equilibrium shifts continuously. If the equilibrium is such that hydroxyapatite is being dissolved, the result is demineralization and a carious condition. On the other hand, if the equilibrium is such that hydroxyapatite is being formed, remineralization occurs.

It is well known that fluoride ions can enhance the natural remineralization process, and this is one of the accepted mechanisms by which fluoride dentifrices protect against caries. Hydroxyapatite reacts with the fluoride ion and is thereby converted into fluoridated hydroxyapatite. Fluoridated hydroxyapatite is less soluble in an acid medium than is hydroxyapatite. Consequently, after a fluoride application, the tooth is better protected from the acid surges which initiate the caries process.

However, the efficacy of fluoride-containing dentifrices to remineralize teeth is limited by the modes levels of free calcium and inorganic orthophosphate ions present in saliva. The concentration of free calcium ions in saliva is especially limited. For example, the concentration of free calcium ions in parotid saliva varies from about 0.9 to about 1.5 millimoles per liter (36–60 parts per million (ppm)). On the other hand, the concentration of free inorganic orthophosphate ions in parotid saliva varies from about 3 to about 9 millimoles per liter (300–850 ppm) depending on the flow of the saliva. Since calcium hydroxyapatite and fluoroapatite contain a calcium-to-phosphate ion ratio of about 5:3, remineralization is most severely limited by the calcium ion levels in the saliva.

Thus, it would be desirable to provide a fluoride-containing dentifrice which could increase the concentration of free calcium cations available for use in the remineralization/mineralization process.

One way to increase the concentration of free calcium cations available for remineralization and/or mineralization would be to add a water-soluble or partially water-soluble calcium salt to the fluoride-containing dentifrice. However, the addition of a calcium compound to a fluoride-containing dentifrice is not a simple matter. Calcium ions react with fluoride ions to form insoluble calcium fluoride. The information of calcium fluoride removes free fluoride anions from the aqueous composition used to remineralize and/or mineralize the teeth. Thus, the premature formation of calcium fluoride in the composition used to treat the teeth inhibits the anticariogenic and remineralizing/mineralizing effects of the fluoride.

Compositions and methods designed to prevent the premature formation of calcium fluoride in dentifrice compositions are known in the art. Reference is made, for example, to U.S. Pat. Nos. 5,476,647 (Chow et al.); 4,283,385 (Dhabhar et al.); 4,923,683 (Sakuma et al.); 4,565,691 (Jackson); and 4,460,565 (Weststrate et al.).

The Chow et al. patent teaches a two-part dentifrice product containing a soluble calcium source in one part and a soluble fluoride source in the other part, wherein reaction between the calcium and fluoride sources is avoided by incorporating a soluble calcium-complexing anion into the calcium part.

The Dhabhar et al. patent teaches a dentifrice containing soluble fluoride and a calcium carbonate or calcium phosphate abrasive, wherein reaction between the fluoride and the abrasive is inhibited by the incorporation of an ethylenediaminetetraacetic acid or sodium salt thereof into the dentifrice.

The Sakuma et al. patent discloses that the reaction between a hydroxyapatite compound and a fluoride compound in a dentifrice composition can be prevented by either storing the hydroxyapatite and fluoride compounds in separate receptacles or by coating or encapsulating one or both of the hydroxyapatite and fluoride compounds.

In the Jackson patent, reaction between a water-soluble ionic fluoride and an ionic calcium-containing abrasive in a dentifrice composition is reduced or prevented by including in the dentifrice composition a water-soluble ionic agent containing the anionic counter ions of the ionic abrasive and metal cations capable of forming a water-soluble fluoride.

The Weststrate et al. patent teaches that a dentifrice composition containing two or more fluorine compounds, at least one soluble salt producing phosphate ions and at least one substance providing calcium ions, wherein inactivation of the fluoride and phosphate ions by the calcium ions is avoided by using specific calcium complexes as the source of calcium ions. Such calcium complexes include the calcium salts of organic acids, e.g., the calcium salts of citric acid, adipic acid, and tartaric acid. Calcium-enriched minerals such as calcium zeolite and calcium apofyllite are also suitable.

A drawback to the processes taught in the aforementioned patents to Chow et al., Dhabhar et al. Sakuma et al. and Weststrate et al., is that the chelating, sequestering or otherwise supplying of calcium in bound form, e.g., hydroxyapatite, ties up the calcium and reduces its availability for remineralization when applied to the teeth.

A drawback to the processes taught in the aforementioned patents to Jackson, and Schumann et al. is that providing the fluoride in complexed or bound form or even in the form of sodium monofluorophosphate reduces the availability of the fluoride for remineralization when applied to the teeth.

As stated previously herein, the amount of inorganic orthophosphate ions in parotid saliva is substantially grater than the amount of calcium ions in the saliva. Since hydroxyapatite contains a 5:3 ration of calcium ions to inorganic orthophosphate ions and further because it is desirable to avoid premature formation of calcium phosphate in the dentifrice aqueous composition used to remineralize and/or mineralize the teeth, it would be desirable to provide a fluoride-containing dentifrice product which increases the concentration of free calcium ions in the remineralizing/mineralizing aqueous composition used to treat the teeth but which does not increase the level of free inorganic orthophosphate ions already present in the saliva. In other words, it would be desirable to provide a dentifrice product which contains fluoride and calcium compounds but which is substantially free of water-soluble inorganic orthophosphates.

Dentifrice compositions containing calcium and fluoride compounds but free of water-soluble inorganic orthophosphate compounds are known in the art. Reference is made, for example, to U.S. Pat. Nos. 4,141,969 and 4,412,983 (both to Mitchell); 3,728,446 (Roberts et al.); 4,265,877 (Tenta); 4,983,379 (Schaeffer); 4,280,822 (Wason); 4,244,707 (Wason); 4,340,584 (Wason); and 5,045,305 (Clarkson et al.).

U.S. Pat. Nos. 4,141,969 and 4,412,983 to Mitchell disclose dental cream compositions containing a dental vehicle, synthetic precipitated silica essentially free of alumina, a fluorine-providing compound and a water-soluble or water-insoluble calcium salt. Phosphate compounds may be present but are not required. Optionally, the dental cream composition may further contain a metallic salt additive to provide metal ions in addition to the calcium ions. Magnesium salts, particularly water-soluble magnesium salts, such as magnesium chloride, are particularly desirable.

U.S. Pat. No. 3,728,446 to Roberts et al. teaches a speckled dentifrice gel composition containing a gel vehicle composed of an aqueous liquid, an alkali metal carboxymethyl cellulose gelling agent, colored particles of the water-insoluble salt of carboxymethyl cellulose and a polyvalent metal, and, optionally, a soluble fluoride compound. The polyvalent metal, which is provided as a water-soluble salt or water-soluble hydroxide, can be calcium, magnesium, strontium, barium, aluminum, gallium, germanium, tin, lead, iron, nickel, zinc, or cadmium. The composition may further contain a polishing agent such as, e.g., magnesium carbonate, calcium carbonate, dicalcium phosphate, tricalcium phosphate, insoluble sodium metaphosphate, calcium pyrophosphate, calcium sulfate and mixture thereof.

U.S. Pat. No. 4,265,877 to Tenta is directed to a chewing gum composition containing a chewing gum base having distributed therein a mixture of sodium fluoride and calcium carbonate in the form of oyster shell. The oyster shell consists of about 97% of calcium carbonate and about 3% of a mixture of trace elements such as magnesium, silicon, manganese, iron, aluminum, copper, sodium, strontium, potassium and zinc.

U.S. Pat. No. 4,983,379 to Schaeffer discloses a dental preparation containing a hydrogen peroxide-containing gel component and a sodium bicarbonate-containing paste component, the gel and paste components being separately stored but capable of being simultaneously dispensed from the package in which they are contained. The paste component may further contain a fluorine compound and cleansing agents such as calcium sulfate, calcium phosphate, calcium carbonate, magnesium carbonate, magnesium silicate, and mixtures of the foregoing. The paste component may also contain a polishing/stabilizing agent such as magnesium oxide. U.S. Pat. Nos. 4,280,822; 4,244,707; and 4,340,584 to Wason disclose dentifrice compositions containing a fluoride-containing therapeutic agent, a polishing agent, a liquid phase, and alkaline earth metal ions. The alkaline earth metal may be calcium, magnesium or strontium, but is preferably calcium. The alkaline earth metal compound is water-soluble and includes the nitrates, oxides, hydroxides and chlorides. The polishing agent may be e.g., dicalcium phosphate, anhydrous dicalcium phosphate, tricalcium phosphate, thermally converted dicalcium phosphate, and insoluble sodium metaphosphate.

U.S. Pat. No. 5,045,305 to Clarkson et al. teaches an oral hygiene product for inhibiting caries, which contains a first composition containing an aqueous solution of calcium ions and a second composition containing an aqueous solution of fluoride ions, wherein the first and second compositions are such that when mixed, rapid precipitation of calcium fluoride occurs. The oral hygiene product maintains a low fluoride ion concentration in the mouth for longer periods than conventional products by the rapid precipitation of calcium fluoride either in the mouth or immediately prior to use. A delivery system providing for physical separation of the two compositions and for simultaneous or sequential delivery of the compositions may also be used.

Although the foregoing patents teach dentifrice compositions containing calcium and fluoride compounds but which are free of water-soluble inorganic orthophosphate compounds, none of the patents teaches or suggests the use or usefulness of the dentifrice product disclosed therein for effecting remineralization and/or mineralization, particularly subsurface remineralization and/or mineralization.

It is desirable to provide dentifrice compositions containing calcium and fluoride compounds and free of water-soluble inorganic orthophosphate compounds, wherein such dentifrice compositions are capable of providing remineralization of subsurface lesions and/or mineralization of exposed dentinal tubules.

Accordingly, it is a primary object of this invention to provide dentifrice products and methods which are capable of providing faster remineralization of subsurface lesions and faster mineralization of exposed dentinal tubules.

A further object of this invention is to provide a fluoride-containing dentifrice product for remineralizing subsurface lesions and/or mineralizing exposed dentinal tubules, wherein the dentifrice product further contains a source of calcium cations and is capable of adding calcium cations to the aqueous saliva composition used to treat the teeth.

A still further object of this invention is to provide a dentifrice product for remineralizing subsurface lesions and/ or mineralizing exposed dentinal tubules, wherein the dentifrice product contains a source of fluoride ions and a source of calcium ions, wherein reaction between the fluoride and calcium sources to form calcium fluoride in the aqueous saliva composition used to treat the teeth is substantially delayed for a period of several minutes.

Another object of this invention is to provide a dentifrice product for remineralizing subsurface lesions and/or mineralizing exposed dentinal tubules, wherein the dentifrice product contains a source of fluoride ions and a source of calcium ions but is substantially free of soluble inorganic orthophosphates.

Yet another object of this invention is to provide a product which has the foregoing characteristics and which is easily usable by the consumer and not differing significantly, in flavor and appearance, form customary dental cosmetics.

A further object of this invention is to provide a method for remineralizing subsurface lesions and/or mineralizing exposed dentinal tubules by means of a product having the aforementioned characteristics.

These and other objects which are achieved according to the present invention can be readily discerned from the following description.

SUMMARY OF THE INVENTION

The present invention is based on the discovery that, in an aqueous composition, the presence of a particular amount of at least one water-soluble or partially water-soluble magnesium compound can significantly delay the reaction between a water-soluble or partially water-soluble calcium compound and a water-soluble fluoride compound to form calcium fluoride if the magnesium and calcium compounds are combined with one another prior to being combined with the fluoride compound. Thus, under appropriate conditions, if the calcium and magnesium compounds are first combined, fluoride ions can be introduced into the system without loss of free fluoride anions for up to several minutes.

Accordingly, one embodiment of the present invention is directed to a two-art dentifrice product which is substantially free of soluble inorganic orthophosphates and which is capable of remineralizing subsurface lesions and/or mineralizing exposed dentinal tubules in teeth, containing:

(A) a discrete cationic part containing at least one water-soluble and/or partially water-soluble calcium compound and a fluoride-protecting amount of at least one water-soluble and/or partially water-soluble magnesium compound, and (B) a discrete anionic part containing at least one water-soluble fluoride compound, the cationic and anionic parts being disposed separate from one another in the product;

wherein the cationic and anionic parts are simultaneously releasable from the product;

further wherein the cationic and anionic parts each have a pH in eater such that a mixed aqueous composition formed by mixing the cationic and anionic parts with (i) saliva or (ii) water and saliva has a pH of from about 4.0 to about 10.0.

Another embodiment of the present invention is directed to a two-part dentifrice product for remineralizing subsurface lesions and/or mineralizing exposed dentinal tubules, containing:

(A) a discrete cationic part containing at least one water-soluble and/or partially water-soluble calcium compound and a fluoride-protecting amount of at least one water-soluble and/or partially water-soluble magnesium compound, and (B) a discrete anionic part containing at least one water-soluble fluoride compound and a minor amount of at least one water-soluble inorganic orthophosphate compound, the cationic and anionic parts being disposed separate from one another in the product;

wherein the cationic and anionic parts are simultaneously releasable from the product;

further wherein the cationic and anionic parts each have a pH in water such that a mixed aqueous composition formed by mixing the cationic and anionic parts with (i) saliva or (ii) water and saliva has a pH of greater than about 4.0 to about 10.0.

A further embodiment of this invention is directed to a two-part dentifrice product for remineralizing subsurface lesions and/or mineralizing exposed dentinal tubules, containing:

(A) a discrete cationic part containing at least one water-soluble and/or partially water-soluble calcium compound and a fluoride-protecting amount of at least one water-soluble and/or partially water-soluble magnesium compound, and (B) a discrete anionic part containing at least one water-soluble fluoride compound, the cationic and anionic parts being disposed separate from one another in the product;

wherein the product is substantially devoid of water-soluble inorganic orthophosphate compounds;

further wherein the cationic and anionic parts are simultaneously releasable from the product;

further wherein the cationic and anionic parts each have a pH in water such that a mixed aqueous composition formed by mixing the cationic and anionic parts with (i) saliva or (ii) water and saliva has a pH of from about 4.0 to about 10.0.

The present invention is further directed to a method for remineralizing at least one subsurface lesion and/or mineralizing at least one exposed dentinal tubule in at least one tooth, involving the steps of:

(1) providing (i) a cationic composition containing at least one water-soluble or partially water-soluble calcium compound and a fluoride-protecting amount of at least one water-soluble and/or partially water-soluble magnesium compound, and (ii) an anionic composition containing at least one water-soluble fluoride compound;

(2) mixing the cationic and anionic compositions with (i) saliva or (ii) water and saliva to form a mixed aqueous composition having a pH of from about 4.0 to about 10.0 and containing calcium cations provided by the calcium compound, magnesium cations provided by the magnesium compound, fluoride anions provided by the fluoride compound and inorganic orthophosphate anions provided by the saliva; and (3) promptly applying the mixed aqueous composition to a surface of the tooth for a period of time sufficient to permit the cations and anions to diffuse through the tooth to the subsurface lesion and/or the exposed dentinal tubule, wherein the cations and anions react to form an insoluble precipitate in the subsurface lesion and/or in or on the exposed dentinal tubule, thereby remineralizing the subsurface lesion and/or mineralizing the exposed tubule.

By providing the mixed aqueous composition used to treat the teeth with a higher concentration of free calcium cations, the products of this invention provide faster remineralization and/or mineralization. Furthermore, by adding such calcium cations while inhibiting the formation of insoluble calcium fluoride, the products of this invention provide faster remineralization and/or mineralization without sacrificing the degree of remineralization and/or mineralization achieved with fluoride.

In addition, by providing a product which is free of soluble inorganic orthophosphates and which increases the concentration of free calcium cations without significantly lowering the concentration of free fluoride anions in the remineralizing/mineralizing aqueous composition, the present invention provides effective subsurface remineralization/mineralization at a faster rate without increasing the risk of premature formation of calcium phosphate in the remineralizing/mineralizing composition.

Furthermore, the present invention provides dentifrice products capable of effecting remineralization of subsurface lesions and/or mineralization of exposed dentinal tubules, wherein the dentifrice products are easily usable by the consumer and do not differ significantly, in flavor and appearance, from customary dental cosmetics.

DETAILED DESCRIPTION OF THE INVENTION

The present invention provides dentifrice products and methods for remineralizing subsurface lesions in teeth and for mineralizing exposed dentinal tubules in teeth.

As used herein, the term "dentifrice" or "dentifrices" refers to products which remain in the mouth for a relatively short period of time, in which they are intimately contacted with substantially all surfaces of the teeth, and are then removed. Non-limiting examples of such products include toothpastes, prophylactic pastes, tooth polishes, gels, professional gels and other products applied by dentists, as well as mouth washes, rinses, dental flosses, chewing gums, lozenges, tablets, edible food products, and the like.

In one preferred embodiment, the products of this invention are formulated as two discrete parts, i.e., a cationic part and an anionic part. The cationic part contains at least one water-soluble and/or partially water-soluble calcium compound and a fluoride-protecting amount of at least one water-soluble and/or partially water-soluble magnesium compound. The anionic part contains at least one water-soluble fluoride compound.

In another embodiment, the products of this invention are formulated as an anhydrous product in which the calcium and magnesium compounds are prevented from reacting during storage by the lack of available water. The ingredients may be further protected by coating or encapsulation techniques. In a paste, gel or liquid formulation, the liquid carrier may be a non-aqueous solvent, preferably a non-aqueous solvent which is water-soluble or water-dispersible.

As used herein with respect to the amount of the magnesium compound, the term "fluoride-protecting amount" means that amount of the magnesium compound which substantially delays reaction between the calcium and fluoride compounds in the mixed aqueous composition to form calcium fluoride, wherein the delay in such reaction is for a period of time sufficient to allow a sufficient number of the calcium cations and fluoride anions to diffuse through the tooth to the subsurface lesion and/or the exposed dentinal tubule to effect substantial subsurface remineralization and/or mineralization. Preferably, such delay in reaction between the calcium and fluoride compounds to form calcium fluoride is at least about 10 seconds, and more preferably from about 10 seconds to about 3 minutes.

In accordance with an important aspect of this invention, the calcium and magnesium compounds are first mixed with one another before being mixed with the fluoride compound. In this way, the magnesium cations are able to "protect" the fluoride anions from the calcium cations for a period of time so as to substantially delay the formation of the sparingly soluble calcium fluoride. The delay in calcium fluoride formation allows the calcium cations added by the products of this invention to increase the rate of remineralization and/or mineralization rather than inactivate the soluble fluoride ions.

In the dentifrice products of this invention, the cationic and anionic parts are kept separate from one another until the product is to be used. In other words, the cationic and anionic parts coexist in the products of this invention in an unmixed state with respect to one another. Alternatively, the cationic and anionic parts can be prevented from reacting on storage by supplying them in an anhydrous mixture.

As stated above, the cationic part used in the product of this invention contains at least one water-soluble and/or partially water-soluble calcium compound and at least one water-soluble and/or partially water-soluble magnesium compound, while the anionic part contains at least one water-soluble fluoride compound.

As used herein, the term "partially water-soluble" with respect to the partially water-soluble calcium compound which can be used in the cationic part of the product of this invention refers to a calcium compound having a solubility which is greater than that of dicalcium phosphate dihydrate in an aqueous solution having a pH of about 7.0 and a temperature of about 25° C. but which is less than that solubility which would release more than about 1400 ppm of calcium cations in such aqueous solution. In an aqueous solution having a pH of about 7.0 at a temperature of about 25° C., dicalcium phosphate dihydrate can release up to about 40 ppm of calcium cations by weight of the aqueous solution. Thus, calcium compounds useful in the cationic part of the product of this invention include calcium salts having a solubility in water such that the salt is capable of releasing more than about 40 ppm but no more than about 1400 ppm, preferably from about 100 ppm to no more than about 1400 ppm, of calcium cations by weight of an aqueous solution having a pH of about 7.0 at a temperature of about 25° C.

In addition, the term "partially water-soluble" with respect to the partially water-soluble magnesium compound which can be used in the cationic part of the product of this invention refers to a magnesium compound having a solubility such that in an aqueous solution having a pH of about 7.0 and a temperature of about 25° C., the magnesium compound is capable of releasing more than about 40 ppm but no more than about 1400 ppm of magnesium cations, preferably from about 100 ppm to no more than about 1400 ppm of magnesium cations, by weight of the aqueous solution.

Furthermore, the term "water-soluble" as used herein with respect to the water-soluble calcium, magnesium and fluoride compounds which can be used in the present invention refers to a solubility such that the compound is capable of releasing at least about 1400 ppm by weight of ions into an aqueous solution having a temperature of about 25° C. and a pH of about 7.0.

Water-soluble calcium salts useful in the product of this invention include, for example, calcium chloride, calcium lactate, calcium nitrate, calcium acetate, and calcium gluconate.

Non-limiting examples of calcium salts of partial water-solubility suitable for use in this invention include calcium sulfate, anhydrous calcium sulfate, calcium sulfate hemihydrate, calcium sulfate dihydrate, calcium malate, calcium tartrate, calcium malonate, calcium succinate, and mixtures of the foregoing. Calcium sulfate is preferred.

The partially water-soluble calcium salt component of the products of this invention can be prepared in situ, for example, by preparing mixtures of an acid such as, e.g., tartaric acid, and a water-soluble calcium salt such as, e.g., calcium nitrate, and adjusting the pH as needed.

In the present invention, the principle known as the "common ion effect" can be used to control the solubility of the partially water-soluble calcium salt used in the present invention and to optimize calcium release and fluoride stability. To achieve the common ion effect, a salt can be added to the product or solution of this invention wherein the anion of the salt is the same as the anion present in the calcium salt used in the particular product or solution. In the present invention, the sodium, potassium and ammonium salts are preferred for use to achieve the common ion effect. However, an anion which is part of another functional ingredient may also be added. For example, the use of magnesium sulfate in a calcium sulfate-based formulation would supply at least some of the needed sulfate anion.

Mixtures of water-soluble and partially water-soluble calcium salts may be used in the cationic part of the product of this invention.

As stated previously herein, the product of this invention further contains a fluoride-protecting amount of at least one water-soluble and/or partially water-soluble magnesium compound in the cationic part of the product. The specific amount of the magnesium compound needed to protect the fluoride will generally depend on the solubility of the particular calcium compound used in the cationic part. In general, the more soluble the calcium compound, the greater the amount of magnesium compound is needed to protect the fluoride, while the less soluble the calcium compound, the lower the amount of magnesium compound is needed to protect the fluoride. If the calcium compound is water-soluble, the fluoride-protecting amount of the magnesium compound will preferably be that amount sufficient to provide an active magnesium ion concentration of at least about 0.05%, more preferably at least about 0.10% and most preferably from about 0.15% to about 0.5%, by weight based on the combined weight of the cationic and anionic parts. If the calcium compound is partially water-soluble, the fluoride-protecting amount of the magnesium compound will preferably be that amount sufficient to provide an active magnesium ion concentration of at least about 0.02%, more preferably at least about 0.05% and most preferably from about 0.07% to about 0.2%, by weight based on the combined weight of the cationic and anionic parts.

Magnesium compounds suitable for use in the cationic part of the product of this invention include, for example, magnesium acetate, magnesium ammonium sulfate, magnesium benzoate, magnesium bromide, magnesium borate, magnesium citrate, magnesium chloride, magnesium chloride hexahydrate, magnesium gluconate, magnesium hydroxide, magnesium iodide, magnesium propionate, magnesium D-lactate, magnesium DL-lactate, magnesium phenolsulfonate, magnesium sulfate, magnesium nitrate, and magnesium tartrate. Preferred magnesium compounds are magnesium chloride and magnesium acetate. Magnesium oxide may also be used. However, because magnesium oxide is very insoluble in water, it is preferably used in combination with an acid, an acid salt, or one or more buffers (e.g., a bicarbonate, which would reduce the pH of the magnesium oxide), so as to render the magnesium oxide partially water-soluble and therefore useful in the present invention.

Suitable water-soluble fluoride compounds for use in the present invention include the alkali metal or ammonium fluorides such as sodium, potassium, lithium or ammonium fluoride; tin fluoride; indium fluoride; zirconium fluoride; copper fluoride; nickel fluoride; palladium fluoride; fluorozirconates such as sodium, potassium or ammonium fluorozirconate or tin fluorozirconate; fluorosilicates; fluoroborates; and fluorostannites. Although not preferred, fluorophosphates, such as sodium fluorophosphate, potassium fluorophosphate and ammonium fluorophosphate, are also suitable for use in the present invention.

Sodium fluoride and stannous fluoride are the preferred fluoride compounds for use in the present invention.

Organic fluorides, such as the known amine fluorides, are also suitable for use in the products of the present invention.

The cationic and anionic parts of the products of this invention each have a pH in water such that the mixed aqueous composition formed by mixing the two parts with saliva or with water and saliva has a pH ranging from about 4.0 to about 10.0, preferably from about 5.0 to about 9.0, more preferably from about 5.5 to about 8.5.

With the inorganic-orthophosphate-free embodiment of the dentifrice product of this invention, the mixed aqueous composition used to treat the teeth in the present invention is composed of calcium cations released by the calcium compound(s), magnesium cations released by the magnesium compound(s), fluoride anions released by the fluoride compound(s), and inorganic orthophosphate anions provided by the saliva.

As mentioned previously herein, in the products of this invention, the cationic and anionic parts are kept separate from one another until the product is to be used. Separation of the two parts can be achieved by various ways.

For instance, the cationic and anionic parts may be separated by a physical barrier such as, for example, when the two parts are disposed in separate compartments of a two-compartment container, e.g., two-compartment tube or two-compartment aerosol can. In this embodiment, the two parts are kept separate from one another during storage but are preferably dispensed simultaneously with one another from the container.

The cationic and anionic parts of the products of this invention may also be kept separate from each other by disposing the parts as separate layers in a multilayer product, for example, a two-layer mouthwash, a two-layer chewing gum, and the like.

It is also possible to employ an emulsion or dispersion wherein the cationic part and the anionic part are present in different phases.

It is further possible to provide the cationic part, the anionic part or both parts with a coating (that is to say, encapsulate it), this coating being such as only to release the active substance through the action of heat or through mechanical action. Examples of suitable encapsulation materials include, e.g., shellac; waxes; fats; vinylpyridine; alkyl vinylpyridine and polymers/copolymers of other vinyl monomers; ethyl cellulose, benzyl cellulose, cellulose acetobutyrate and other cellulose derivatives; polyvinyl acetal diethylaminoacetate and dimethylaminoethyl methacrylate/methyl methacrylate copolymers; and the like.

In addition, separation of the cationic and anionic parts may be achieved by disposing one part in an aqueous medium and the other part in a non-aqueous, water-insoluble medium, wherein the aqueous medium and the water-insoluble mediums are capable of simultaneously releasing the cationic and anionic parts. Examples of suitable non-aqueous mediums include non-aqueous solvents such as, e.g., ethyl alcohol, glycerine, propylene glycol and polyethylene oxide. Preferably, the non-aqueous, hydrophilic liquid carrier medium is a polyethylene oxide having a molecular weight of about 400 (also known under the designation "Carbowax 400").

Separation may also be achieved by disposing the two parts in a single carrier medium, wherein the single carrier medium is non-aqueous and hydrophilic and capable of simultaneously releasing the two parts upon contact with water.

Yet another way to separate the cationic and anionic parts is to dispose the cationic part in a first carrier medium and the anionic part in a second carrier medium, wherein the first carrier medium is composed of a material in which the anionic part is insoluble but the cationic part is soluble, further wherein the second carrier medium is composed of a material in which the cationic part is insoluble but the anionic part is soluble.

In the products of this invention, the cationic and anionic parts may both be aqueous, e.g., may both be in the form of aqueous solutions. Alternatively, one or both of the cationic and anionic parts may be non-aqueous. While completely aqueous compositions are preferred in the present invention for application to the teeth, non-aqueous solvents may be employed in combination with water and/or saliva to form an aqueous/non-aqueous medium. Suitable non-aqueous solvents include, e.g., ethyl alcohol, glycerine, propylene glycol and polyethylene oxide. Solvent systems suitable for use in the present invention are those which are safe for use in the mouth.

In another embodiment of the product of this invention, the anionic part of the product may contain a minor amount of a water-soluble inorganic orthophosphate salt. As used herein with respect to the amount of the water-soluble inorganic orthophosphate compound which may be present in the anionic part of the product of this invention, the term "minor amount" means that amount of the water-soluble inorganic orthophosphate compound such that a mixture of the water-soluble inorganic orthophosphate salt with the saliva with which it is combined to form the mixed aqueous composition has a concentration of inorganic orthophosphate ions of at least about 300 ppm but no higher than about 850 ppm. This concentration range is the average concentration range of inorganic orthophosphate anions in parotid saliva.

Suitable water-soluble inorganic orthophosphate compounds for use in the present invention include, for example, the alkali salts and ammonium salts of orthophosphoric acid, such as, e.g., potassium, sodium or ammonium orthophosphate; monopotassium phosphate; dipotassium phosphate; tripotassium phosphate; monosodium phosphate; disodium phosphate and trisodium phosphate.

In another embodiment of the product of this invention, the product is substantially devoid of water-soluble inorganic orthophosphate compounds but may contain a water-insoluble phosphate compound as an abrasive and/or polishing agent.

Suitable insoluble phosphate polishing agents include various calcium phosphates such as, for example, dicalcium phosphate, tricalcium phosphate, calcium pyrophosphate, beta-phase calcium pyrophosphate, dicalcium phosphate dihydrate, anhydrous calcium phosphate, sodium metaphosphate, and the like.

If a water-insoluble calcium phosphate polishing agent is used in the present invention, such polishing agent is preferably kept separate from the fluoride, particularly if the fluoride is sodium or stannous fluoride, so as to prevent formation of insoluble calcium fluoride during storage.

As stated previously herein, the cationic and anionic parts are mixed either in the oral cavity or immediately prior to their introduction into the oral cavity. If the cationic and anionic parts are both aqueous compositions, the two parts may be mixed together outside of the oral cavity and the resulting mixture then immediately introduced into the oral cavity to be admixed with the saliva, the resulting saliva composition then being applied to the teeth. Alternatively, the two parts may be introduced into the oral cavity, where the two parts are combined simultaneously with one another and with the saliva to form the saliva composition used to treat the teeth.

With a toothpaste, gel, and the like, mixing is achieved on the surface to the teeth while brushing.

If one or both of the cationic and anionic parts are encapsulated or coated, the two parts may be simultaneously introduced into the oral cavity, where they are chewed or sucked in the presence of saliva to form a saliva composition which is used to treat the teeth.

As stated previously herein, the mixed aqueous composition formed by mixing the cationic and anionic parts with water and/or saliva has a pH of from about 4.0 to about 10.0, preferably from about 5.0 to about 9.0, more preferably from about 5.5 to about 8.5. At a pH within such range, enough of the calcium cations, magnesium cations, fluoride anions and inorganic orthophosphate anions remain soluble for the period of time required to remineralize the subsurface lesions and/or mineralize the exposed tubules of the dental enamel. If the mixed aqueous composition has a pH below about 3, demineralization will occur rapidly. A pH below about 2.5 is undesirable from a safety standpoint.

The pH of the mixed aqueous composition may be adjusted to the desired pH by methods well known in the art. The pH may be lowered by the addition of any acid which is safe for use in the oral cavity and which yields the desired pH at the amount employed. Examples of suitable acids include acetic acid, phosphoric acid, citric acid and malic acid.

The mixed aqueous composition and the insoluble precipitate formed therefrom in the present invention must both have acceptable levels of toxicity (i.e., the particular ions, in the amounts used in the remineralization/mineralization process, must be non-toxic) and must both be otherwise compatible in the oral environment.

In the present invention, the cationic and anionic parts are delivered simultaneously to the tooth surfaces by means of the mixed aqueous composition. In this way, ions which effect remineralization and/or mineralization can be absorbed simultaneously by the dental enamel and their reaction causes re-hardening of the demineralized subsurface areas of the teeth and mineralization of the exposed dentinal tubules of the teeth.

An important feature of the present invention lies in the mixing of the anionic and cationic parts and the "promptly applying" of the resulting mixed composition to the tooth. The term "promptly" as used herein with respect to the time period between mixing of the anionic and cationic parts in the presence of (i) saliva or (ii) water and saliva and the application of the mixed aqueous composition to the teeth means that time period which is sufficient to allow a sufficient amount of the cations and anions to diffuse through the surface of the tooth to the dentin and/or subsurface of the tooth so as to achieve substantial subsurface remineralization and/or mineralization. Preferably, the time period between the mixing of the cationic and anionic parts and the application of the resulting mixed aqueous composition to the teeth should not exceed 1 minute, and preferably is less than 1 minute. The period of time of exposure of the mixed aqueous composition to the teeth must be great enough to allow the aforementioned diffusion of the ions into the demineralized subsurface to occur. Typically, at least about ten seconds are required for such diffusion. Preferably, the mixed aqueous composition is applied to the teeth for from about 10 seconds to about 3 minutes.

The pH of the mixed aqueous composition will rise due to natural factors after its introduction into the oral cavity. Precipitation of the cations and anions occurs during this rise in pH but after the ions have diffused into the demineralized tooth enamel.

In order to effect subsurface remineralization and/or mineralization, a therapeutic amount of the desired cations and anions is used in the mouth. The composition placed in the mouth should be such as to raise the calcium content in the saliva above the normal levels of about 50 ppm. Preferably, the calcium content should be raised to above about 100 ppm, more preferably above about 200 ppm, and most preferably above about 400 ppm. The composition placed in the mouth should also be such as to raise the fluoride content in the saliva to above about 0.1 ppm, preferably above about 1 ppm, more preferably above about 10 ppm, and most preferably above about 100 ppm.

The remineralizing-mineralizing precipitate formed in the present invention is a calcium phosphate or a hydroxyapatite (the natural constituent of tooth enamel) with incorporated fluoride and magnesium ions. Because of the presence of the fluoride ions in the mixed aqueous composition used in this invention, the remineralized enamel is more resistant to demineralization than was the original enamel. Therefore, use of the mixed aqueous composition in accordance with the present invention not only remineralizes the enamel but also renders such enamel more resistant to subsequent demineralization than was the original enamel.

The products of this invention can be used in conventional forms, for example, in solution, paste or gel form or as a solid substance. The only requirement is that until use of the product, the part containing the calcium and magnesium compounds remains separate from the part containing the fluoride compound.

In preferred embodiments, the products of this invention are in the form of toothpastes, prophylactic pastes, tooth polishes, gels, professional gels, creams and other products applied by dentists, as well as mouthwashes, rinses, dental flosses, chewing gums, lozenges, tablets, edible food products, and the like.

The products of this invention may contain conventional additives for dental and oral cosmetics. For example, the products may contain flavoring agents, aroma agents, surfactants, astringents and preservatives.

Where one or both of the cationic and anionic parts are in the form of a paste, such pastes usually contain conventional substances of polishing agents. Suitable polishing agents include, e.g., calcium carbonate and various calcium phosphates such as, for example, dicalcium phosphate, tricalcium phosphate, calcium pyrophosphate, and the like. Suitable abrasives which can be used in the present invention include, for example, silica xerogels. Other conventional toothpaste abrasives can be used in the products of this invention, such as, e.g., beta-phase calcium pyrophosphate, dicalcium phosphate dihydrate, anhydrous calcium phosphate, calcium carbonate, zirconium silicate, and thermosetting polymerized resins. Silica aerogels and insoluble metaphosphates such as insoluble sodium metaphosphate can also be used. Mixtures of abrasives can be also be used. Silica xerogel abrasives are preferred.

The total content of abrasive agent in the dentifrice is variable but will generally be up to about 90% by weight of the total composition. Generally, however, the abrasive will be present in an amount of from about 5% to about 60% by weight, preferably from about 20% to about 50% by weight, and most preferably from about 25% to about 45% by weight.

Where one or both of the cationic and anionic parts are in the form of a transparent gel, the gel-forming agents usually used include known thickeners, e.g., the alkali salts of polyacrylic acid, and also preferentially dehydrated silicon dioxide gels of particle size of 2 to 20 microns and specific surface area of about 200 to 900 square meters per gram.

Any suitable surface active or detersive material may be included in the dentifrice products of this invention. Such materials are desirable to provide additional detersive, foaming and anti-bacterial properties depending upon the specific type of surface active material. These detergents are usually water-soluble organic compounds and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulfate detergents (e.g., sodium coconut fatty acid monoglyceride monosulfate), higher alkyl sulfate (e.g., sodium lauryl sulfate), alkyl aryl sulfonate (e.g., sodium dodecyl benzene sulfonate), higher fatty acid esters of 1,2-dihydroxy propane sulfonate (e.g., sodium coconut fatty acid ester of 1,2-dihydroxy propane sulfonate), and the like.

The various surface active materials may be used in any suitable amount, generally from about 0.05% to about 10% by weight, and preferably from about 0.5% to about 5% by weight of the dentifrice product.

In addition to the active anionic and cationic salts previously described herein, toothpaste, gel and cream products within the scope of this invention preferably further contain sudsing agents, binding agents, and/or humectants. An inorganic thickener such as hydrated silica may also be added.

Suitable sudsing agents for use in the present invention include those which are reasonably stable and which form suds throughout the period of application. Preferably, non-soap anionic or nonionic organic synthetic detergents are employed. Examples of such agents include, e.g., water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonate; salts of $C_{10}$–$C_{18}$ fatty acid amides of taurine, such as sodium N-methyl taurate; salts of $C_{10}$–$C_{18}$ fatty acid esters of isothionic acid; and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material can be added to thicken and provide a desirable consistency to the products of the present invention. Suitable thickening agents include, e.g., water-soluble salts of cellulose ethers, such as, for example, sodium carboxymethyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum.

It is also desirable to include some humectant material in toothpaste or gel embodiments of the present invention to keep such products from hardening. Suitable humectants include, e.g., glycerine, sorbitol, polyethylene glycol, propylene glycol, and other edible polyhydric alcohols, as well as mixtures thereof.

Toothpaste or gel products within the scope of this invention may also contain flavoring agents such as, for example, oil of wintergreen, oil of peppermint, oil of spearmint, oil of sassafras, and oil of clove.

Toothpaste or gel products of the present invention may also contain sweetening agents such as, e.g., saccharin, dextrose, levulose, sodium cyclamate, and aspartame. Mixtures of sugar with a sweetener, e.g., sucralose, are also contemplated for use in the present invention.

It is also possible to manufacture the dentifrice products of the present invention in the form of a transparent or translucent gel. This is accomplished by matching the refractive index of the water-humectant system with the abrasives and inorganic thickeners if used.

Professional gels can be formulated similar to dentifrices but with higher fluoride contents. Since these products are not designed for cleaning but only as a fluoride application, abrasives and other cleaning agents need not be included in the formulation.

Other products within the scope of this invention include mouthwashes and rinses. Mouthwashes and rinses generally contain an aqueous solution of ethyl alcohol and flavoring materials. The alcohol provides an antibacterial effect, solubilizes the flavoring materials and provides a pleasant mouth feeling. Alcohol-free mouthwashes are now, however, gaining in popularity. Optionally, mouthwashes and rinses also contain additional antibacterial agents and humectants such as glycerine and sorbitol which give a moist feeling to the mouth.

In addition to the anionic and cationic active ingredients discussed previously herein, mouthwashes and rinses preferably contain from about 0 to about 30%, preferably from about 0 to about 20%, by weight of ethyl alcohol; from about 30% to about 90% by weight of water; from about 0 to about 20% by weight of glycerine or other humectant; from about 0 to about 0.1% by weight of an antibacterial agent; from about 0 to about 0.2% by weight of a soluble fluoride source; from about 0.01% to about 0.5% by weight of a sweetening agent; from about 0.01% to about 2.0% by weight of a flavoring agent; and from about 0.1% to about 1% by weight of an emulsifier-surfactant.

Chewable tablets may be formulated in a manner similar to the aforementioned dentifrices. Since the tablets are packaged in a water-free state, the cationic and anionic parts can be safely included in the same tablet. The reaction between the cationic and anionic parts will begin after they are in contact with the saliva through the chewing action.

With respect to toothpastes, gels, creams and the like within the scope of this invention, a plurality of packaging methods may be employed in order to separately contain or store the cationic and anionic parts and provide effective dispensing thereof into the oral cavity.

Thus, the cationic and anionic parts may be simultaneously dispensed from separate collapsible tubes preferably made of plastic, a plastic and metal laminate, etc. For convenience and in order to aid in dispensing substantially equal amounts of the parts, the tubes may be held together by banding or cementing, preferably along the corresponding ventral sides of the tubes.

In another embodiment, the two tubes may be constructed to have abutting, preferably flat, sidewall portions. In the foregoing embodiments, the mouths of the tubes are usually sufficiently close so that sufficient quantities of the cationic and anionic parts of the toothpaste or gel may be simultaneously dispensed directly on the toothbrush with the tubes being capped separately.

Alternatively, another packaging method involves loading the cationic and anionic parts of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and anionic parts, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of the outer tube and the mouth of the inner tube. The closures of this tube-within-a-tube (which can screw on the outer tube or simply be held by pressure) may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement is a pressurized container which is provided with two compartments and two spouts. The internal pressure of the compartments is maintained by a pressurized gas, i.e., nitrogen, at the bottom of each compartment. Operation of a mechanical actuator actuates valves which release the contents of the compartments through the spouts, causing discharge of the paste or gel components onto a brush.

The mouthwash, rinse or similar liquid embodiments are maintained in a manner similar to the pastes or gels in that, during storage, each of the cationic and anionic parts are maintained separate from one another to prevent premature reaction. Upon dispensing, the cationic and anionic parts mix and react in the oral cavity to effect remineralization of dental enamel. The liquid cationic and anionic parts can therefore be stored each in separate compartments of a dual-compartment dispenser. The dispenser usually includes a closure system containing, for example, an inclined crown portion, at least two pouring spouts extending upwardly from an upper surface of the crown portion, and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve a window function for gauging the amounts of liquid remaining in the dispenser. The walls of the containers can be scribed or otherwise calibrated to assist in dispensing the correct remineralizing amount of the mixed aqueous composition.

The following Examples illustrate the invention. In the Examples and elsewhere herein, parts and percentages are by weight unless otherwise stated.

EXPERIMENTAL

The examples below illustrate the effect which the presence of a magnesium salt in the cationic part of the products of this invention has on the level of free fluoride retained in the mixture formed by mixing the cationic and anionic parts of the products.

Examples 1–7 and Controls A–C

In Examples 1–7 and Controls A–C, ten (10) two-part products were prepared having the formulations shown in Table I below. In each example and control, the cationic part (i.e., part A) of the product contained partially water-soluble calcium sulfate as the calcium salt. The anionic part of each product contained sodium fluoride as the fluoride salt and was free of water-soluble inorganic orthophosphates. The cationic part of the products prepared in Examples 1–7 further contained magnesium chloride hexahydrate, while the cationic part of the products of Controls A–C did not contain a magnesium compound or any other divalent metal compound. In each of the Examples and Controls, the cationic and anionic parts of the products were combined and mixed for one minute with deionized water in a ratio of one part product to three parts water. The solutions were filtered to remove undissolved fluoride. The concentration of free fluoride in the filtered solution was measured and the results set forth in Table I. Table I recites the concentration of the magnesium chloride hexahydrate. The active magnesium ion concentration of the recited amount of the magnesium chloride hexahydrate can be calculated by dividing the atomic weight of magnesium (i.e., 24) by the molecular weight of magnesium chloride hexahydrate (i.e., 203) and multiplying the resulting value by the recited concentration of the magnesium chloride hexahydrate. Thus, a concentration of 0.8% by weight of magnesium chloride hexahydrate provides an active magnesium ion concentration of about 0.1% by weight; a concentration of 0.4% by weight of magnesium chloride hexahydrate provides an active magnesium ion concentration of about 0.05% by weight; and a concentration of 0.2% by weight of magnesium chloride hexahydrate provides an active magnesium ion concentration of about 0.025% by weight.

TABLE I

Examples 1–7 and Controls A–C: Formulations

| Ingredient | 1 | 2 | 3 | 4 |
|---|---|---|---|---|
| Part A | | | | |
| Glycerine | 10 | 5 | 10 | 5 |
| PEG 8 | 1 | 1 | 1 | 1 |
| Methyl Paraben | 0.025 | 0.025 | 0.025 | 0.025 |
| Propyl Paraben | 0.025 | 0.025 | 0.025 | 0.025 |
| CMC | 0.5 | 0.9 | 0.5 | 0.9 |
| Water | 20.15 | 20.35 | 20.15 | 20.35 |
| Sorbitol | 5 | 10 | 5 | 10 |
| Sodium Saccharin | 0.3 | 0.3 | 0.3 | 0.3 |
| $MgCl_2 \cdot 6H_2O$ | 0.8 | 0.2 | 0.8 | 0.2 |
| Titanium Dioxide | 0.1 | 0.1 | 0.1 | 0.1 |
| Calcium Sulfate | 2.85 | 2.85 | 2.85 | 2.85 |
| Hydrated Silica Abrasive | 4.75 | 4.75 | 4.75 | 4.75 |
| Hydrated Silica Thickener | 3 | 3 | 3 | 3 |
| Flavor | 0.5 | 0.5 | 0.5 | 0.5 |
| Tween 20 | 0.5 | 0.5 | 0.5 | 0.5 |
| Sodium Lauryl Sulfate | 0.5 | 0.5 | 0.5 | 0.5 |
| Part B | | | | |
| Glycerine | 5.75 | 5.75 | 5.75 | 5.75 |
| NaOH | 0 | 0 | 0.2 | 0.2 |
| Acetic Acid | 0 | 0 | 0.3 | 0.3 |
| Lactic Acid | 0 | 0 | 0 | 0 |
| CMC | 0.45 | 0.45 | 0.45 | 0.45 |
| Water | 12 | 12 | 11.5 | 11.5 |
| Sorbitol | 21.65 | 21.65 | 21.65 | 21.65 |
| Sodium Saccharin | 0.15 | 0.15 | 0.15 | 0.15 |
| NaF | 0.25 | 0.25 | 0.25 | 0.25 |
| Hydrated Silica Abrasive | 7 | 7 | 7 | 7 |
| Hydrated Silica Thickener | 1.5 | 1.5 | 1.5 | 1.5 |
| Flavor | 0.5 | 0.5 | 0.5 | 0.5 |
| Sodium Lauryl Sulfate | 0.75 | 0.75 | 0.75 | 0.75 |
| TOTAL | 100 | 100 | 100 | 100 |
| pH | 6.72 | 6.72 | 7.9 | 7.9 |
| Free Fluoride (ppm) | 1037 | 212 | 1113 | 354 |

| Ingredient | 5 | 6 | 7 |
|---|---|---|---|
| Part A | | | |
| Glycerine | 10 | 10 | 5 |
| PEG 8 | 1 | 1 | 1 |
| Methyl Paraben | 0.025 | 0.025 | 0.025 |
| Propyl Paraben | 0.025 | 0.025 | 0.025 |
| CMC | 0.5 | 0.5 | 0.9 |
| Water | 20.15 | 20.55 | 20.35 |
| Sorbitol | 5 | 5 | 10 |
| Sodium Saccharin | 0.3 | 0.3 | 0.3 |
| $MgCl_2 \cdot 6H_2O$ | 0.8 | 0.4 | 0.2 |
| Titanium Dioxide | 0.1 | 0.1 | 0.1 |
| Calcium Sulfate | 2.85 | 2.85 | 2.85 |
| Hydrated Silica Abrasive | 4.75 | 4.75 | 4.75 |
| Hydrated Silica Thickener | 3 | 3 | 3 |
| Flavor | 0.5 | 0.5 | 0.5 |
| Tween 20 | 0.5 | 0.5 | 0.5 |
| Sodium Lauryl Sulfate | 0.5 | 0.5 | 0.5 |
| Part B | | | |
| Glycerine | 5.75 | 5.75 | 5.75 |
| NaOH | 0.025 | 0.025 | 0.025 |
| Acetic Acid | 0 | 0 | 0 |
| Lactic Acid | 0.1 | 0.1 | 0.1 |
| CMC | 0.45 | 0.45 | 0.45 |
| Water | 11.875 | 11.875 | 11.875 |
| Sorbitol | 21.65 | 21.65 | 21.65 |
| Sodium Saccharin | 0.15 | 0.15 | 0.15 |
| NaF | 0.25 | 0.25 | 0.25 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 6.41 | 6.41 | 6.41 |
| Free Fluoride (ppm) | 997 | 380 | 204 |

| Ingredient | A | B | C |
|---|---|---|---|
| Part A | | | |
| Glycerine | 10 | 10 | 10 |
| PEG 8 | 1 | 1 | 1 |
| Methyl Paraben | 0.025 | 0.025 | 0.025 |
| Propyl Paraben | 0.025 | 0.025 | 0.025 |
| CMC | 0.5 | 0.5 | 0.5 |
| Water | 20.95 | 20.95 | 20.95 |
| Sorbitol | 5 | 5 | 5 |
| Sodium Saccharin | 0.3 | 0.3 | 0.3 |
| $MgCl_2 \cdot 6H_2O$ | 0 | 0 | 0 |
| Titanium Dioxide | 0.1 | 0.1 | 0.1 |
| Calcium Sulfate | 2.85 | 2.85 | 2.85 |
| Hydrated Silica Abrasive | 4.75 | 4.75 | 4.75 |
| Hydrated Silica Thickener | 3 | 3 | 3 |
| Flavor | 0.5 | 0.5 | 0.5 |
| Tween 20 | 0.5 | 0.5 | 0.5 |
| Sodium Lauryl Sulfate | 0.5 | 0.5 | 0.5 |
| Part B | | | |
| Glycerine | 5.75 | 5.75 | 5.75 |
| NaOH | 0 | 0.2 | 0.025 |
| Acetic Acid | 0 | 0.3 | 0 |
| Lactic Acid | 0 | 0 | 0.1 |
| CMC | 0.45 | 0.45 | 0.45 |
| Water | 12 | 11.5 | 11.875 |
| Sorbitol | 21.65 | 21.65 | 21.65 |
| Sodium Saccharin | 0.15 | 0.15 | 0.15 |
| NaF | 0.25 | 0.25 | 0.25 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 6.72 | 7.9 | 6.41 |
| Free Fluoride (ppm) | 113 | 118 | 159 |

The results presented in Table I show that, in Examples 1–7, the free fluoride levels in the mixed aqueous solution increased with increasing magnesium content. In Controls A–C, which used no magnesium in the cationic part of the products, the mixed aqueous solution had much lower free fluoride levels than similar mixtures containing magnesium chloride. Thus, Examples 1–7 and Controls A–C illustrate the advantage of using magnesium in the cationic part of the product to retain relatively high levels of free fluoride in the mixed aqueous solution formed when the cationic and anionic parts are mixed.

Examples 8–15 and Controls D–F

Examples 8–15 and Controls D–F show the effect on free fluoride levels in the mixed aqueous solution when the cationic part contains water-soluble calcium lactate and magnesium chloride. In Examples 8–15 and Controls D–F, eleven (11) two-part products were prepared having the formulations shown in Table II below. In Examples 8–15 and controls D–F, part B was free of orthophosphate inorganic orthophosphate compounds and contained sodium fluoride as the fluoride salt, and part A contained calcium lactate. In Examples 8–15, the cationic part further contained magnesium chloride, while, in Controls D and E, the cationic part did not contain magnesium chloride or any other divalent metal salt. The cationic part of the Control F product contained strontium chloride. In each of the Examples and Controls, the cationic and anionic parts of the products were combined and mixed for one minute with deionized water in a ratio of one part product to three parts water. The solutions were filtered to remove undissolved fluoride. The concentration of free fluoride in the filtered solution was measured and the results set forth in Table II. The free fluoride levels remaining after the two parts of each product were mixed are set forth in Table II.

Table II recites the concentration of the magnesium chloride hexahydrate. The active magnesium ion concentration of the recited amount of the magnesium chloride hexahydrate can be calculated as described hereinabove. Thus, a concentration of 0.25% by weight of magnesium chloride hexahydrate provides an active magnesium ion concentration of about 0.03% by weight; a concentration of 0.5% by weight of magnesium chloride hexahydrate provides an active magnesium ion concentration of about 0.06% by weight; a concentration of 1.0% by weight of magnesium chloride hexahydrate provides an active magnesium ion concentration of about 0.12% by weight; a concentration of 1.5% by weight of magnesium chloride hexahydrate provides an active magnesium ion concentration of about 0.18% by weight; a concentration of 2.0% by weight of magnesium chloride hexahydrate provides an active magnesium ion concentration of about 0.24% by weight.

TABLE II

Examples 8–15 and Controls D–F: Formulations

| Ingredient | Example No. Concentration (parts by weight) | | | |
|---|---|---|---|---|
| | 8 | 9 | 10 | 11 |
| Part A | | | | |
| Glycerine | 6.5 | 6.5 | 6.5 | 6.5 |
| PEG 8 | 0 | 0 | 0 | 0 |
| Methyl Paraben | 0.025 | 0.025 | 0.025 | 0.025 |
| Propyl Paraben | 0.025 | 0.025 | 0.025 | 0.025 |
| CMC | 0.5 | 0.5 | 0.5 | 0.5 |
| Water | 18.9 | 18.4 | 17.9 | 17.4 |
| Sorbitol | 10 | 10 | 10 | 10 |
| Sodium Saccharin | 0.3 | 0.3 | 0.3 | 0.3 |
| $MgCl_2 \cdot 6H_2O$ | 0.5 | 1 | 1.5 | 2 |
| Strontium Chloride | 0 | 0 | 0 | 0 |
| Calcium lactate | 1.75 | 1.75 | 1.75 | 1.75 |
| Hydrated Silica Abrasive | 7 | 7 | 7 | 7 |
| Hydrated Silica Thickener | 3 | 3 | 3 | 3 |
| Flavor | 0.5 | 0.5 | 0.5 | 0.5 |
| Tween 20 | 0.5 | 0.5 | 0.5 | 0.5 |
| Sodium Lauryl Sulfate | 0.5 | 0.5 | 0.5 | 0.5 |
| Part B | | | | |
| Glycerine | 5.75 | 5.75 | 5.75 | 5.75 |
| NaOH | 0.2 | 0.2 | 0.2 | 0.2 |
| Acetic Acid | 0.3 | 0.3 | 0.3 | 0.3 |
| Lactic Acid | 0 | 0 | 0 | 0 |
| CMC | 0.45 | 0.45 | 0.45 | 0.45 |
| Water | 11.5 | 11.5 | 11.5 | 11.5 |
| Sorbitol | 21.65 | 21.65 | 21.65 | 21.65 |
| Sodium Saccharin | 0.15 | 0.15 | 0.15 | 0.15 |
| NaF | 0.25 | 0.25 | 0.25 | 0.25 |
| Hydrated Silica Abrasive | 7 | 7 | 7 | 7 |
| Hydrated Silica Thickener | 1.5 | 1.5 | 1.5 | 1.5 |
| Flavor | 0.5 | 0.5 | 0.5 | 0.5 |
| Sodium Lauryl Sulfate | 0.75 | 0.75 | 0.75 | 0.75 |
| TOTAL | 100 | 100 | 100 | 100 |
| pH | 7.68 | 7.68 | 7.68 | 7.68 |
| Free Fluoride (ppm) | 260 | 522 | 806 | 845 |

| Ingredient | Example No. Concentration (parts by weight) | | | |
|---|---|---|---|---|
| | 12 | 13 | 14 | 15 |
| Part A | | | | |
| Glycerine | 6.5 | 6.5 | 6.5 | 6.5 |
| PEG 8 | 0 | 0 | 0 | 0 |
| Methyl Paraben | 0.025 | 0.025 | 0.025 | 0.025 |
| Propyl Paraben | 0.025 | 0.025 | 0.025 | 0.025 |
| CMC | 0.5 | 0.5 | 0.5 | 0.5 |
| Water | 19.4 | 19.4 | 19.4 | 19.4 |
| Sorbitol | 10 | 10 | 10 | 10 |
| Sodium Saccharin | 0.3 | 0.3 | 0.3 | 0.3 |
| $MgCl_2 \cdot 6H_2O$ | 0.5 | 1 | 1.5 | 2 |
| Strontium Chloride | 0 | 0 | 0 | 0 |
| Calcium lactate | 1.75 | 1.75 | 1.75 | 1.75 |
| Hydrated Silica Abrasive | 7 | 7 | 7 | 7 |
| Hydrated Silica Thickener | 3 | 3 | 3 | 3 |
| Flavor | 0.5 | 0.5 | 0.5 | 0.5 |
| Tween 20 | 0.5 | 0.5 | 0.5 | 0.5 |
| Sodium Lauryl Sulfate | 0.5 | 0.5 | 0.5 | 0.5 |
| Part B | | | | |
| Glycerine | 5.75 | 5.75 | 5.75 | 5.75 |
| NaOH | 0.025 | 0.025 | 0.025 | 0.025 |
| Acetic Acid | 0 | 0 | 0 | 0 |
| Lactic Acid | 0.1 | 0.1 | 0.1 | 0.1 |
| CNC | 0.45 | 0.45 | 0.45 | 0.45 |
| Water | 11.875 | 11.875 | 11.875 | 11.875 |
| Sorbitol | 21.65 | 21.65 | 21.65 | 21.65 |
| Sodium Saccharin | 0.15 | 0.15 | 0.15 | 0.15 |
| NaF | 0.25 | 0.25 | 0.25 | 0.25 |
| Hydrated Silica Abrasive | 7 | 7 | 7 | 7 |
| Hydrated Silica Thickener | 1.5 | 1.5 | 1.5 | 1.5 |
| Flavor | 0.5 | 0.5 | 0.5 | 0.5 |
| Sodium Lauryl Sulfate | 0.75 | 0.75 | 0.75 | 0.75 |
| TOTAL | 100.5 | 101 | 101.5 | 102 |
| pH | 6.23 | 6.23 | 6.23 | 6.23 |
| Free Fluoride (ppm) | 286 | 415 | 744 | 793 |

| Ingredient | Controls Concentration (parts by weight) | | |
|---|---|---|---|
| | D | E | F |
| Part A | | | |
| Glycerine | 6.5 | 6.5 | 6.5 |
| PEG 8 | 0 | 0 | 0 |
| Methyl paraben | 0.025 | 0.025 | 0.025 |
| Propyl Paraben | 0.025 | 0.025 | 0.025 |
| CMC | 0.5 | 0.5 | 0.5 |
| Water | 19.4 | 19.4 | 18.75 |
| Sorbitol | 10 | 10 | 10 |
| Sodium Saccharin | 0.3 | 0.3 | 0.3 |
| $MgCl_2 \cdot 6H_2O$ | 0 | 0 | 0 |
| Strontium Chloride | 0 | 0 | 0.65 |
| Calcium lactate | 1.75 | 1.75 | 1.75 |
| Hydrated Silica Abrasive | 7 | 7 | 7 |
| Hydrated Silica Thickener | 3 | 3 | 3 |
| Flavor | 0.5 | 0.5 | 0.5 |
| Tween 20 | 0.5 | 0.5 | 0.5 |
| Sodium Lauryl Sulfate | 0.5 | 0.5 | 0.5 |

TABLE II-continued

Examples 8–15 and Controls D–F: Formulations

Part B

| | | | |
|---|---|---|---|
| Glycerine | 5.75 | 5.75 | 5.75 |
| NaOH | 0.2 | 0.025 | 0.2 |
| Acetic Acid | 0.3 | 0 | 0.3 |
| Lactic Acid | 0 | 0.1 | 0 |
| CMC | 0.45 | 0.45 | 0.45 |
| Water | 11.5 | 11.875 | 11.5 |
| Sorbitol | 21.65 | 21.65 | 21.65 |
| Sodium Saccharin | 0.15 | 0.15 | 0.15 |
| NaF | 0.25 | 0.25 | 0.25 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 7.68 | 6.23 | 7.68 |
| Free Fluoride (ppm) | 143 | 140 | 158 |

The results presented in Table II show that the level of free fluoride in the mixed aqueous solution increased with increasing magnesium content in the cationic part of the product. However, even with the use of the soluble calcium lactate at an amount of 1.75 parts by weight of the total weight of the cationic and anionic parts, not all of the fluoride can be maintained in free form in the mixture. However, Examples 8–15 show that at a magnesium chloride concentration of 1.5% by weight and above, the level of free fluoride in the mixed aqueous solution is sufficient to meet the FDA monograph on anti-caries products. Control F, which used strontium chloride instead of magnesium chloride, shows that strontium chloride did not appreciably increase the level of free fluoride in the mixed aqueous solution formed therein. Thus, Examples 8–15 and Controls D–F also show that although magnesium and strontium are both divalent metals, magnesium has a relatively high fluoride-protecting ability whereas strontium has little or no fluoride-protecting ability.

Examples 16 and 17 and Controls G–J

Examples 16 and 17 and Controls G–J compare the free-fluoride protecting ability of a magnesium salt with the free-fluoride protecting ability of various other divalent metal salts. In Examples 16 and 17 and Controls G–J, six (6) two-part products were prepared, having the formulations set forth in Table III below. In Examples 16 and 17, the calcium salt used was water-soluble calcium acetate, and the divalent metal salt used was magnesium chloride. In Control G, no divalent metal salt was used. In Control H, the divalent metal salt was strontium chloride. In Control I, zinc acetate was used as the divalent metal salt. In Control J, the divalent metal salt was stannous chloride. The ionic concentrations of the strontium, zinc and stannous ions used in Controls H–J, respectively, were equivalent to the ionic concentration of the magnesium used in Example 16. In each of the Examples and Controls, the cationic and anionic parts of the products were combined and mixed for one minute with deionized water in a ratio of one part product to three parts water. The solutions were filtered to remove undissolved fluoride. The concentration of free fluoride in the filtered solution was measured and the results set forth in Table III. The free fluoride levels remaining after the two parts of each product were mixed are also set forth in Table III.

Table III recites the concentration of the magnesium chloride hexahydrate. The active magnesium ion concentration of the recited amount of the magnesium chloride hexahydrate can be calculated as described hereinabove.

TABLE III

Examples 16 and 17 and Comparative Examples G–J: Formulations

Example No./Control Concentration (parts by weight)

| Ingredient | 16 | 17 | G |
|---|---|---|---|
| Part A | | | |
| Glycerine | 8.25 | 8.25 | 8.25 |
| Methyl Paraben | 0.025 | 0.025 | 0.025 |
| Propyl Paraben | 0.025 | 0.025 | 0.025 |
| CMC | 0.5 | 0.5 | 0.5 |
| Water | 18.4 | 17.9 | 19.4 |
| Sorbitol | 10 | 10 | 10 |
| Sodium Saccharin | 0.3 | 0.3 | 0.3 |
| $MgCl_2 \cdot 6H_2O$ | 1 | 1.5 | 0 |
| Strontium Chloride | 0 | 0 | 0 |
| Zinc Acetate | 0 | 0 | 0 |
| Stannous Chloride | 0 | 0 | 0 |
| Calcium Acetate | 0.5 | 0.5 | 0.5 |
| Hydrated Silica Abrasive | 7 | 7 | 7 |
| Hydrated Silica Thickener | 3 | 3 | 3 |
| Flavor | 0.5 | 0.5 | 0.5 |
| Tween 20 | 0.5 | 0.5 | 0.5 |
| Part B | | | |
| Glycerine | 5.75 | 5.75 | 5.75 |
| NaOH | 0.2 | 0.2 | 0.2 |
| Acetic Acid | 0.3 | 0.3 | 0.3 |
| Lactic Acid | 0 | 0 | 0 |
| CMC | 0.45 | 0.45 | 0.45 |
| Water | 11.5 | 11.5 | 11.5 |
| Sorbitol | 21.65 | 21.65 | 21.65 |
| Sodium Saccharin | 0.15 | 0.15 | 0.15 |
| NaF | 0.25 | 0.25 | 0.25 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 7.47 | 7.45 | 7.6 |
| Free Fluoride (ppm) | 864 | 837 | 391 |

Control Concentration (parts by weight)

| Ingredient | H | I | J |
|---|---|---|---|
| Part A | | | |
| Glycerine | 8.25 | 8.25 | 8.25 |
| Methyl Paraben | 0.025 | 0.025 | 0.025 |
| Propyl Paraben | 0.025 | 0.025 | 0.025 |
| CMC | 0.5 | 0.5 | 0.5 |
| Water | 18.1 | 18.3 | 18.3 |
| Sorbitol | 10 | 10 | 10 |
| Sodium Saccharin | 0.3 | 0.3 | 0.3 |
| $MgCl_2 \cdot H_2O$ | 0 | 0 | 0 |
| Strontium Chloride | 1.3 | 0 | 0 |
| Zinc Acetate | 0 | 1.1 | 0 |
| Stannous Chloride | 0 | 0 | 1.1 |
| Calcium Acetate | 0.5 | 0.5 | 0.5 |
| Hydrated Silica Abrasive | 7 | 7 | 7 |
| Hydrated Silica Thickener | 3 | 3 | 3 |
| Flavor | 0.5 | 0.5 | 0.5 |
| Tween 20 | 0.5 | 0.5 | 0.5 |
| Part B | | | |
| Glycerine | 5.75 | 5.75 | 5.75 |
| NaOH | 0.2 | 0.2 | 0.2 |
| Acetic Acid | 0.3 | 0.3 | 0.3 |
| Lactic Acid | 0 | 0 | 0 |
| CMC | 0.45 | 0.45 | 0.45 |
| Water | 11.5 | 11.5 | 11.5 |
| Sorbitol | 21.65 | 21.65 | 21.65 |
| Sodium Saccharin | 0.15 | 0.15 | 0.15 |

TABLE III-continued

Examples 16 and 17 and Comparative Examples G–J: Formulations

| | | | |
|---|---|---|---|
| NaF | 0.25 | 0.25 | 0.25 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 7.5 | 6.38 | 4.76 |
| Free Fluoride (ppm) | 294 | 366 | 372 |

As can be seen from Table III, magnesium chloride exhibited relatively high fluoride-protecting ability. However, neither strontium chloride, zinc acetate nor stannous chloride exhibited any fluoride-protecting ability. In fact, the use of these divalent metal salts (Controls H–J) actually resulted in a concentration of free fluoride in the mixed aqueous solution which was lower than that found in a mixed aqueous solution formed with no divalent metal salt (Control G). Thus, Examples 16 and 17 and Controls G–J show that although magnesium, strontium, zinc and tin are all divalent metals, magnesium has relatively high fluoride-protecting ability under the conditions existing in Examples 16 and 17, whereas strontium, zinc and tin have no fluoride-protecting ability under the same conditions.

Example 18–21 and Control K

Examples 18–21 and Control K illustrate the effect on free fluoride levels when the cationic part of the product contains sodium monofluorophosphate (sodium MFP) while the anionic part contains sodium fluoride. In Examples 18–21 and Control K, five (5) two-part products were prepared, having the formulations shown in Table IV below. In each product, the cationic part contained sodium monofluorophosphate (MFP) and the anionic part contained sodium fluoride. In Examples 18–21, the cationic part also contained magnesium chloride. In Control K, the cationic part did not contain magnesium chloride or any other divalent metal salt. In the Examples and Control, the cationic and anionic parts of the products were combined and mixed for one minute with deionized water in a ratio of one part product to three parts water. The solutions were filtered to remove undissolved fluoride. The concentration of free fluoride in the filtered solution was measured and the results set forth in Table IV. The free fluoride levels and the free calcium levels present in the mixed aqueous solutions formed by combining the cationic and anionic parts in each example and control are set forth in Table IV.

Table IV recites the concentration of the magnesium chloride hexahydrate. The active magnesium ion concentration of the recited amount of the magnesium chloride hexahydrate can be calculated as described hereinabove.

TABLE IV

Examples 18–21 and Control K: Formulations

| | Example No. Concentration (parts by weight) | | |
|---|---|---|---|
| Ingredient | 18 | 19 | 20 |
| Part A | | | |
| Glycerine | 6.5 | 6.5 | 6.5 |
| Methyl Paraben | 0.025 | 0.025 | 0.025 |
| Propyl Paraben | 0.025 | 0.025 | 0.025 |
| CMC | 0.5 | 0.5 | 0.5 |
| Water | 18.98 | 18.48 | 17.98 |
| Sorbitol | 10 | 10 | 10 |
| Sodium Saccharin | 0.3 | 0.3 | 0.3 |
| $MgCl_2 \cdot 6H_2O$ | 0.5 | 1 | 1.5 |
| Calcium Lactate | 1.75 | 1.75 | 1.75 |
| Hydrated Silica Abrasive | 7 | 7 | 7 |
| Hydrated Silica Thickener | 3 | 3 | 3 |
| Sodium MFP | 0.42 | 0.42 | 0.42 |
| Flavor | 0.5 | 0.5 | 0.5 |
| Tween 20 | 0.5 | 0.5 | 0.5 |
| Part B | | | |
| Glycerine | 5.75 | 5.75 | 5.75 |
| NaOH | 0.2 | 0.2 | 0.2 |
| Acetic Acid | 0.3 | 0.3 | 0.3 |
| CMC | 0.45 | 0.45 | 0.45 |
| Water | 11.625 | 11.625 | 11.625 |
| Sorbitol | 21.65 | 21.65 | 21.65 |
| Sodium Saccharin | 0.15 | 0.15 | 0.15 |
| NaF | 0.125 | 0.125 | 0.125 |
| Hydrated Silica Abrasive | 7 | 7 | 7 |
| Hydrated Silica Thickener | 1.5 | 1.5 | 1.5 |
| Flavor | 0.5 | 0.5 | 0.5 |
| Sodium Lauryl Sulfate | 0.75 | 0.75 | 0.75 |
| TOTAL | 100 | 100 | 100 |
| pH | 6.22 | 6.22 | 6.2 |
| Free Fluoride (ppm) | 181 | 291 | 528 |
| Free Calcium (ppm) | 1649 | 1944 | 1993 |
| Total Active Fluoride (ppm) | 751 | 861 | 1098 |

| | Example No./Control Concentration (parts by weight) | |
|---|---|---|
| Ingredient | 21 | K |
| Part A | | |
| Glycerine | 6.5 | 6.5 |
| Methyl Paraben | 0.025 | 0.025 |
| Propyl Paraben | 0.025 | 0.025 |
| CMC | 0.5 | 0.5 |
| Water | 17.48 | 19.48 |
| Sorbitol | 10 | 10 |
| Sodium Saccharin | 0.3 | 0.3 |
| $MgCl_2 \cdot 6H_2O$ | 2 | 0 |
| Calcium Lactate | 1.75 | 1.75 |
| Hydrated Silica Abrasive | 7 | 7 |
| Hydrated Silica Thickener | 3 | 3 |
| Sodium MFP | 0.42 | 0.42 |
| Flavor | 0.5 | 0.5 |
| Tween 20 | 0.5 | 0.5 |
| Part B | | |
| Glycerine | 5.75 | 5.75 |
| NaOH | 0.2 | 0.2 |
| Acetic Acid | 0.3 | 0.3 |
| CMC | 0.45 | 0.45 |
| Water | 11.625 | 11.625 |
| Sorbitol | 21.65 | 21.65 |
| Sodium Saccharin | 0.15 | 0.15 |
| NaF | 0.125 | 0.125 |
| Hydrated Silica Abrasive | 7 | 7 |
| Hydrated Silica Thickener | 1.5 | 1.5 |
| Flavor | 0.5 | 0.5 |
| Sodium Lauryl Sulfate | 0.75 | 0.75 |
| TOTAL | 100 | 100 |
| pH | 6.19 | 6.27 |
| Free Fluoride (ppm) | 635 | 166 |
| Free Calcium (ppm) | 2146 | 1410 |
| Total Active Fluoride (ppm) | 1205 | 736 |

It should be noted that because monofluorophosphate is reasonable stable in the presence of calcium ions, monofluorophosphate can be included in formulations containing free calcium ions as was done in the Part A formulations shown in Table IV. However, the test method used in the fluoride analyses is such as to only include fluoride as the free ion, not as monofluorophosphate. The sodium monofluorophospate added to each formulations adds an additional 570 ppm active fluoride to the system. The total active fluoride content was determined by adding 570 to the determined free fluoride content.

Monofluorophosphate ion is considered to be active fluoride for the purposes of anti-cavity protection. However, while in this form, it is much less effective in promoting remineralization than fluoride ion itself.

The results presented in Table IV show that magnesium chloride additions results in increased levels of free fluoride. Table IV also shows that despite the maintenance of higher free fluoride levels, the addition of magnesium ion did not adversely reduce the free calcium concentration. In fact, higher free calcium concentrations were obtained in the presence of magnesium. This indicates that the magnesium will have a beneficial effect on remineralization and mineralization.

What is claimed is:

1. A two-part product capable of remineralizing subsurface lesions and/or mineralizing exposed dentinal tubules in teeth, comprising:
    (A) a discrete cationic part containing at least one water-soluble and/or partially water-soluble calcium compound and a fluoride-protecting amount of at least one water-soluble and/or partially water-soluble magnesium compound, and
    (B) a discrete anionic part containing at least one water-soluble fluoride compound, the cationic and anionic parts being disposed separate from one another in the product;
        wherein the cationic and anionic parts further being simultaneously releasable from the product;
        further wherein the cationic and anionic parts each have a pH in water such that a mixed aqueous composition formed by mixing the cationic and anionic parts with water and/or saliva has a pH of from about 4.0 to about 10.0;
        further wherein said product is free of water-soluble inorganic orthophosphates.

2. A product according to claim 1, wherein the cationic and anionic parts each have a pH in water such that the mixed aqueous composition has a pH of from about 5.0 to about 9.0.

3. A product according to claim 1, wherein said at least one calcium salt is a partially water-soluble calcium salt selected from the group consisting of calcium sulfate, anhydrous calcium sulfate, calcium sulfate hemihydrate, calcium sulfate dihydrate, calcium malate, calcium tartrate, calcium malonate, calcium succinate, and mixtures of the foregoing.

4. A product according to claim 3, wherein the fluoride-protecting amount of said at least one water-soluble and/or partially water-soluble magnesium compound is such as to provide an active magnesium ion concentration of at least about 0.02% by weight based on the combined weight of the cationic and anionic parts.

5. A product according to claim 4, wherein the fluoride-protecting amount of said at least one water-soluble and/or partially water-soluble magnesium compound is such as to provide an active magnesium ion concentration of at least about 0.05% by weight based on the combined weight of the cationic and anionic parts.

6. A product according to claim 4, wherein the fluoride-protecting amount of said at least one water-soluble and/or partially water-soluble magnesium compound is such as to provide an active magnesium ion concentration of at least about 0.07% to about 0.20% by weight based on the combined weight of the cationic and anionic parts.

7. A product according to claim 1, wherein said at least one calcium salt is a water-soluble calcium salt selected from the group consisting of calcium chloride, calcium nitrate, calcium acetate, calcium lactate and calcium gluconate, and mixtures of the foregoing.

8. A product according to claim 7, wherein the fluoride-protecting amount of said at least one water-soluble and/or partially water-soluble magnesium compound is such as to provide an active magnesium ion concentration of at least about 0.05% by weight based on the combined weight of the cationic and anionic parts.

9. A product according to claim 7, wherein the fluoride-protecting amount of said at least one water-soluble and/or partially water-soluble magnesium compound is such as to provide an active magnesium ion concentration of at least about 0.10% by weight based on the combined weight of the cationic and anionic parts.

10. A product according to claim 7, wherein the fluoride-protecting amount of said at least one water-soluble and/or partially water-soluble magnesium compound is such as to provide an active magnesium ion concentration of at least about 0.15% to about 0.50% by weight based on the combined weight of the cationic and anionic parts.

11. A product according to claim 1, wherein said magnesium salt is selected from the group consisting of magnesium acetate, magnesium ammonium sulfate, magnesium benzoate, magnesium bromide, magnesium borate, magnesium citrate, magnesium chloride, magnesium gluconate, magnesium hydroxide, magnesium iodide, magnesium propionate, magnesium D-lactate, magnesium DL-lactate, magnesium phenolsulfonate, magnesium sulfate, magnesium nitrate, and magnesium tartrate.

12. A product according to claim 1, wherein said magnesium salt is magnesium chloride or magnesium acetate.

13. A product according to claim 1, wherein said at least one water-soluble fluoride salt is an alkali metal fluoride or an ammonium fluoride.

14. A product according to claim 1, wherein said at least one water-soluble fluoride salt is sodium fluoride or stannous fluoride.

15. A product according to claim 1, wherein said cationic and anionic parts are disposed in separate compartments of a two-compartment container.

16. A product according to claim 1, wherein one of said cationic and anionic parts is disposed in an aqueous medium and the other of said cationic and anionic parts is disposed in a non-aqueous, hydrophilic medium.

17. A product according to claim 1, wherein one or both of said cationic and anionic parts are encapsulated.

18. A product according to claim 16, wherein said one or both of said cationic and anionic parts are encapsulated with a material selected from the group consisting of shellac, waxes, fats, vinylpyridine, alkyl vinylpyridine, ethyl cellulose, benzyl cellulose, cellulose acetobutyrate, polyvinyl acetal diethylaminoacetate, dimethylaminoethyl methacrylate/methyl, methacrylate copolymers, polyethylene, polyvinyl chloride, rubber, and polyvinyl acetate.

19. A product according to claim 1, wherein said cationic part is disposed in a first carrier medium and said anionic part is disposed in a second carrier medium, wherein said first carrier medium is comprised of a material in which said anionic part is insoluble, further wherein said second carrier medium is comprised of a material in which said cationic part is insoluble.

20. A product according to claim 1, wherein said cationic and anionic parts are each aqueous solutions.

21. A product according to claim 1, wherein one or both of said cationic and anionic parts is non-aqueous.

22. A product according to claim 1, wherein said product is selected from the group consisting of toothpastes, prophylactic pastes, tooth polishes, gels, professional gels, mouthwashes, rinses, dental flosses, chewing gums, lozenges, tablets, and edible food products.

23. A two-part product capable of remineralizing subsurface lesions and/or mineralizing exposed dentinal tubules in teeth, comprising:
 (A) a discrete cationic part containing at least one water-soluble and/or partially water-soluble calcium compound and a fluoride-protecting amount of at least one water-soluble and/or partially water-soluble magnesium compound, and
 (B) a discrete anionic part containing at least one water-soluble fluoride compound and a minor amount of at least one water-soluble inorganic orthophosphate compound; the cationic and anionic parts being disposed separate from one another in the product;
  wherein the cationic and anionic parts are simultaneously releasable from the product;
  further wherein the cationic and anionic parts each have a pH in water such that a mixed aqueous composition formed by mixing the cationic and anionic parts with water and/or saliva has a pH of greater than about 4.0 to about 10.0.

24. A product according to claim 23, wherein said cationic and anionic parts each have a pH in water such that said mixed aqueous composition has a pH of from about 5.0 to about 9.0.

25. A two-part product capable of remineralizing subsurface lesions and/or mineralizing exposed dentinal tubules in teeth, comprising:
 (A) a discrete cationic part containing at least one water-soluble and/or partially water-soluble calcium compound and a fluoride-protecting amount of at least one water-soluble and/or partially water-soluble magnesium compound, and
 (B) a discrete anionic part containing at least one water-soluble fluoride compound; the cationic and anionic parts being disposed in the product in an unmixed state with respect to one another;
  wherein said product is devoid of water-soluble inorganic orthophosphate compounds;
  further wherein the cationic and anionic parts are simultaneously releasable from the product;
  further wherein the cationic and anionic parts each have a pH in water such that a mixed aqueous composition formed by mixing the cationic and anionic parts with water and/or saliva has a pH of from greater than about 4.0 to about 10.0.

26. A product according to claim 25, wherein said cationic and anionic parts each have a pH in water such that said mixed aqueous composition has a pH of from about 5.0 to about 9.0.

27. A product according to claim 25, wherein said anionic part further comprises an abrasive.

28. A method for remineralizing at least one subsurface lesion and/or mineralizing at least one exposed dentinal tubule in at least one tooth, comprising the steps of:
 (1) providing a cationic composition comprising at least one water-soluble or partially water-soluble calcium compound and a fluoride-protecting amount of at least one water-soluble and/or partially water-soluble magnesium compound, and providing an anionic composition comprising at least one water-soluble fluoride compound, the cationic and anionic compositions each being devoid of water-soluble inorganic orthophosphate compounds;
 (2) mixing said cationic and anionic compositions together with (i) saliva or (ii) with water and saliva to form a mixed aqueous composition having a pH of from about 4.0 to about 10.0 and comprising calcium cations released by said calcium compound, magnesium cations released by said magnesium compound, fluoride anions released by said fluoride compound, and inorganic orthophosphate anions provided by said saliva;
 (3) promptly applying said mixed aqueous composition to said tooth, thereby simultaneously delivering said calcium and magnesium cations and said fluoride and inorganic orthophosphate anions to said tooth and thereby allowing said cations and anions to simultaneously diffuse through said tooth to said subsurface lesion and/or to said exposed dentinal tubule, said cations and anions reacting to form an insoluble precipitate on said subsurface lesion and/or said exposed dentinal tubule, thereby remineralizing said subsurface lesion and/or mineralizing said exposed dentinal tubule.

* * * * *